United States Patent [19]

Boyer et al.

[11] 4,061,541
[45] Dec. 6, 1977

[54] PREPARATION OF ALKALINE ALPHA-AMYLASE

[75] Inventors: Ernest Wendell Boyer; Morton Blakeman Ingle, both of Elkhart, Ind.

[73] Assignee: Miles Laboratories, Inc., Elkhart, Ind.

[21] Appl. No.: 123,880

[22] Filed: Mar. 12, 1971

[51] Int. Cl.$^2$ ............................................. C07G 7/028
[52] U.S. Cl. .................................. 195/66 R; 195/62; 195/31 R
[58] Field of Search ....................... 195/62, 66, 63, 68, 195/31

[56] References Cited

U.S. PATENT DOCUMENTS 3,634,266    1/1972    Theile et al. ....................... 195/63 X

FOREIGN PATENT DOCUMENTS 2,025,748    10/1970    Germany.

OTHER PUBLICATIONS

Campbell, Jr. L. L., Purification and Properties of an Alpha-Amylase from Facultative Thermophilic Bacteria, Archives of Biochemistry and Biophysics, 1/1955, vol. 54, No. 1, (pp. 154–161).

Nishida et al., Reversibility of Acid–Inactivation of Bacillus Subtilis Alpha-Amylas, Agr. Biol. Chem. vol. 31, No. 6, 1967, pp. (682–693).

Sumner et al., The Enzymes, vol. 1, Part I, Academic Press Inc., N.Y. 1950, pp. (697–702).

*Primary Examiner*—David M. Naff
*Attorney, Agent, or Firm*—Joseph C. Schwalbach; Louis E. Davidson

[57] ABSTRACT

An alpha-amylase enzyme having optimum pH activity under alkaline conditions is produced from Bacillus species NRRL-3881. The enzyme is stable in the presence of chelating agents and is useful in producing maltose-containing products.

1 Claim, No Drawings

PREPARATION OF ALKALINE ALPHA-AMYLASE

BACKGROUND AND PRIOR ART

Amylases are enzymes which are capable of catalyzing the hydrolysis of carbohydrates to form short-chain fragments, such as glucose, maltose, maltotriose and the like. These amylases are useful in liquefaction of starch and are also useful in removal of starch-containing stains from clothing. The prior art amylases have optimum activity under acid conditions and can have their activity impaired by chelating agents. The enzyme activity of such prior art amylases is thus reduced somewhat when they are employed in conjunction with detergents under alkaline conditions.

SUMMARY OF THE INVENTION

A novel amylase, which has optimum activity under alkaline conditions and is stable in the presence of chelating agents, can be prepared by growing under aerobic conditions a culture of *Bacillus* species NRRL B-3381 or mutants thereof in a medium containing appropriate nutrients and then recovering the enzyme therefrom.

DESCRIPTION OF THE INVENTION

The organism useful in the present invention has been classified as a *Bacillus* species according to well-known procedures. It does not fall into any recognized species and is believed to be a new species within the *Bacillus* genus. The particular strain of *Bacillus* species useful in the production of the novel amylase was isolated from dried sludge from a sewage plant. A sample of the strain has been deposited with the Northern Utilization Research and Development Division, Agricultural Research Service of the United States Department of Agriculture, Peoria, Illinois and has been given the identification number NRRL B-3881. This culture is available to the public without restriction.

This strain has the following characteristics:

Vegetative rods: 0.9 to 1.0$\mu$ by 3.0 to 4.0$\mu$; ends rounded; usually in chains (2-6 per chain); not chained on soybean agar; usually actively motile (probably peritrichously flagellated); Gram-positive; has Gram-variable form which is small, twisted, and bent when grown at pH below 8.0.

Sporangia: definitely swollen; clavate.

Spores: 0.5 to 0.8$\mu$ by 1.0 to 1.5$\mu$; oval; terminal to subterminal; refractile; good sporulation only in an alkaline medium which contains starch.

Capsule: extends 0.5 to 0.9$\mu$ from surface of cell.

Colonies: thin or thick depending on the medium; spreading; large colonies (1 cm.) at pH 9.0–10.0, very small colonies at pH 7.0–8.0; opaque; entire.

Additional Characteristics

Tryptone yeast extract dextrose agar, pH 7.0: slow growth; small colonies.

Nutrient broth, pH 9: turbidity light to fair; flocculent to slimy sediment.

Nutrient agar slants with 1.0% $Na_4P_2O_7 \cdot 10 H_2O$: no sporulation; colony shiny; form, irregular; elevated, umbonate; margin, lobate.

Nutrient agar slants, pH 7.0: no growth.

Sodium chloride broth: growth heavy in 12% NaCl with thick pellicle at the surface; growth slow in 15% NaCl with no pellicle at the surface.

Soybean agar slants: growth heavy; cells were not chained; no sporulation.

Hydrolysis of starch: positive; wide zone of hydrolysis.

Production of acetylmethylcarbinol: negative at 37° C.

pH of glucose broth: initial pH 10; final pH 8.98.

Hydrolysis of gelatin: positive; wide zone of hydrolysis.

Hydrolysis of casein: scant, if any, hydrolysis.

Production of indole: negative.

Urease: negative.

Reduction of nitrate to nitrite: negative.

Reduction of methylene blue: positive; reoxidized in 5–7 days.

| Fermentation characteristics at pH 10.0 | | |
|---|---|---|
| Carbohydrate | Growth | Final Color of Medium |
| Glucose | 1+ | Clear |
| Sucrose | 2+ | Clear |
| Lactose | 3+ | Dark yellow brown |
| Maltose | 3+ | Dark yellow brown |
| Mannitol | 4+ | Clear |
| Arabinose | 3+ | Yellow |
| Xylose | 4+ | Yellow |
| Glycerol | 4+ | Light yellow |
| Sorbitol | 2+ | Clear |
| Salicin | 3+ | Clear |
| Control (no carbohydrate) | Slight | Clear |

Acid without gas was produced from all the carbohydrates tested.

It should be understood that the process of the present invention is not limited solely to the use of *Bacillus* species NRRL B-3881, since the natural and artificial mutants thereof can also be employed. Such mutants can be obtained by well-known techniques, such as X-ray and ultraviolet irradiation.

The *Bacillus* species NRRL B-3881 organism is maintained in frozen litmus milk and can be grown in a medium containing appropriate nutrients, such as carbohydrates, nitrogen sources and inorganic salts. Illustrative carbohydrates are corn starch, dextrose, starch syrups, lactose, milk solids, wheat bran, maltose and the like. Illustrative nitrogen sources are soya meal, tryptone, yeast extract, meat extract, amino acids, proteins, ammonium sulfate and the like. Illustrative inorganic salts are calcium chloride, sodium phosphates, potassium phosphates, magnesium sulfate and the like. These carbohydrates, nitrogen sources and inorganic salts are well known in the art.

The organism preferably is grown under submerged aerobic conditions for about 15 to about 25 hours at a temperature from about 25° to about 55° C. The preferred growth temperature is from about 35° to about 46° C. The pH of the growth medium should be from about 8 to about 10 and preferably from 8.5 to 9.0.

The desired amylase of the present invention is present in the fermentation beer outside the bacterial cells which grow during its production and can be recovered in the liquid form by simply filtering off the bacterial cells from the fermentation beer and retaining the filtrate. The resulting enzyme-containing liquid can be concentrated by well-known technqiues or the enzyme can be precipitated and recovered in a solid form by well-known techniques.

The amylase produced by the present process is assayed for enzyme activity in the following manner. A 2.4% starch solution is prepared by mixing 13 grams (dry weight) Lintner soluble starch and 25 ml. distilled water. This mixture is then slowly added to 400 ml. boiling distilled water. The resulting solution is cooled to room temperature and diluted to 500 ml. with distilled water. Equal volume parts of the above starch solution and an aqueous 0.1 molar glycine buffer solution are then mixed to form the starch substrate. The pH of the mixture is then adjusted to 9.2 at 50° C with 5N sodium hydroxide. A dilute hydrochloric acid solution is prepared by adding 1 volume part concentrated HCl to about 90 volume parts distilled water. Dilute to total volume of 100 parts with distilled water. An iodine solution is prepared by mixing 5 ml. concentrated HCl solution, 300 ml. distilled water and 10 ml. of a solution containing 0.2% iodine and 2% potassium iodide and diluting the entire mixture to 500 ml. with distilled water.

In order to carry out the assay a 5 ml. portion of the starch substrate is pipetted into a 25 × 150 mm. test tube. The tube is stoppered and heated at 50° C. for 15 min. A 20 ml. portion of the dilute HCl solution is then added to a separate 25 × 150 mm. test tube and a 10 ml. portion of the iodine solution is added to a third 25 × 150 mm. test tube. A 1 ml. portion of the enzyme solution being assayed is then added to the starch substrate and mixed to form a digest solution. After 15 min. a 1 ml. portion of the digest solution is added to the dilute HCl solution and mixed. A 1 ml. portion of the resulting mixture is then added to the iodine solution and mixed. After 15 min. the optical density of the mixture is measured with a light source having a wavelength of 600 millimicrons. The spectrophotometer is adjusted to zero against distilled water. The enzyme concentration should be such that the change in optical density is not greater than 0.15 in 15 min. A reagent blank is prepared by adding 5 ml. starch substrate and 1 ml. enzyme solution to 120 ml. dilute HCl solution and mixing. A 1 ml. portion of this reagent blank is added to 10 ml of the iodine solution. After 15 min. the optical density of the blank is measured. The enzyme activity in alkaline amylase units per ml. of sample is computed by the following formula:

$$\text{Activity (units/ml.)} = \frac{(OD_{blank} - OD_{sample})(\text{Dilution}) 10^5}{15}$$

The invention is described in more detail in the following examples.

EXAMPLE I

An aqueous inoculum medium was prepared containing on a weight/volume basis: 0.5 percent tryptone, 0.5 percent yeast extract, 0.1 percent dextrose and 0.1 percent $K_2HPO_4$. A 596 ml. portion of the above medium was placed into each of four Fernbach flasks and was sterilized at 250° F. (121° C.) for 20 min. The medium was cooled and 66 ml of a sterile 10 percent (weight/volume basis) solution of sodium sesquicarbonate was added to adjust the pH. Each flask was then inoculated with 1 ml. of a thawed frozen litmus milk culture of Bacillus species NRRL B-3881. The flasks were then placed on a gyrotory shaker operating at 200 RPM and incubated at 39° C. for 18 hours. All the contents of the flasks were then used to inoculate 133 liters of a fermentation medium at a concentration of 2 volume percent inoculum. The aqueous fermentation medium contained (weight/volume basis) 1.5 percent partially hydrolyzed starch syrup, 2 percent soya meal, 0.1 percent calcium chloride, 0.9 percent $Na_2HPO_4$, 0.1 percent antifoam and was sterilized at 250° F. for 30 min. and cooled to 96° F. (36° C.). This medium also contained 1 percent sterile sodium bicarbonate (added aseptically as a 10 percent (weight/volume basis) solution and sufficient sterile 5N sodium hydroxide to adjust the pH to 9.1. The fermentation medium was agitated and sterile air at 4.6 SCFM was passed through the fermentor contents. Fermentation was stopped after 21 hours. The bacterial cells were separated from the fermentation beer which contained 8000 amylase units/ml. The pH was adjusted to 7.5 with diluted HCl and appropriate filter aids were added. The resulting mixture was filtered on a vacuum drum filter. The filtrate was then concentrated about 25 fold using ultrafiltration techniques to produce an enzyme concentrate containing 90,000 amylase units/ml.

The resulting novel amylase has maximum activity at pH 9 to pH 9.2 and at about 50° C. In contrast to this a typical prior art amylase has maximum activity at pH 5.8 to pH 6.5 and at about 60° C. After being held at 32° C and pH 9.2 for one hour in the presence of chelating agents, such as ethylene diamine tetraacetic acid or sodium pyrophosphate, the novel amylase retained all of its amylase activity. Prior art amylases when treated to the same conditions lose about half of their amylase activity.

The novel amylase produced in accordance with the present invention appears to be an endo-amylase (alpha-type amylase) and thus can be useful to produce maltose-containing products from starch. This is shown in the following example.

EXAMPLE II

A portion of the amylase produced in Example I containing 90,000 amylase units/ml. was diluted 1/500 with 0.05 molar glycine buffer solution, and 80 ml. of the resulting solution were added to 250 ml. of an aqueous solution containing 0.0909 percent (weight/volume basis) amylose in 0.05 molar glycine buffer adjusted to pH 9.2 at 50° C. After 100 hours at 50° C. there was an apparent conversion of 75.5 percent of the amylose to maltose and a conversion of 4.6 percent of the amylose to glucose. A small quantity of maltotriose was also produced. Such analyses were carried out by well known procedures.

What is claimed is:

1. A process for the production of an alpha-amylase having maximum activity at a pH value from 9 to 9.2 and at about 50° C. comprising growing under aerobic conditions and at a pH from about 8 to about 10 a culture of Bacillus species NRRL B-3881 in a medium containing appropriate nutrients and then recovering the enzyme therefrom.

* * * * *